(12) United States Patent
Walkenhorst et al.

(10) Patent No.: US 6,726,722 B2
(45) Date of Patent: Apr. 27, 2004

(54) THREADED APPARATUS FOR FUSING ADJACENT BONE STRUCTURE

(75) Inventors: Jared Walkenhorst, Fairfield, CT (US); Herb Cohen, Shelton, CT (US); Lance Middleton, Trumbull, CT (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 10/001,695

(22) Filed: Oct. 24, 2001

(65) Prior Publication Data
US 2002/0049499 A1 Apr. 25, 2002

Related U.S. Application Data
(60) Provisional application No. 60/242,927, filed on Oct. 24, 2000.

(51) Int. Cl.[7] .............................. A61B 17/56; A61F 2/44
(52) U.S. Cl. ...................................... 623/17.16; 606/73
(58) Field of Search ........................... 623/17.16, 17.11; 606/61, 60, 62, 72, 66, 73

(56) References Cited

U.S. PATENT DOCUMENTS

| 4,349,921 A | 9/1982 | Kuntz |
| 4,501,269 A | 2/1985 | Bagby |
| 4,743,256 A | 5/1988 | Brantigan |
| 4,834,757 A | 5/1989 | Brantigan |
| 4,877,020 A | 10/1989 | Vich |
| 4,878,915 A | 11/1989 | Brantigan |
| 4,936,848 A | * 6/1990 | Bagby ..................... 623/17.16 |
| 4,961,740 A | 10/1990 | Ray et al. |
| 5,015,255 A | 5/1991 | Kuslich |
| 5,026,373 A | 6/1991 | Ray et al. |
| 5,171,278 A | 12/1992 | Pisharodi |
| 5,390,683 A | 2/1995 | Pisharodi |
| 5,443,514 A | 8/1995 | Steffee |

(List continued on next page.)

FOREIGN PATENT DOCUMENTS

| FR | 2 742 044 A1 | 12/1995 |
| WO | WO 99/47083 | 3/1999 |
| WO | WO 01/13807 A2 | 3/2001 |
| WO | WO 01/68006 A1 | 3/2001 |

Primary Examiner—Pedro Philogene
Assistant Examiner—David A Bonderer
(74) Attorney, Agent, or Firm—Lerner, David, Littenberg, Krumholz & Mentlik, LLP

(57) ABSTRACT

A fusion implant apparatus for facilitating fusion of adjacent bone structures includes an implant member for positioning between adjacent opposed bone structures. The implant member defines a longitudinal axis and first and second longitudinal ends and has an outer wall dimensioned to engage the opposed bone structures upon positioning therebetween in supporting relation therewith. The outer wall includes at least one thread for facilitating positioning between the opposed bone structures. The implant member has an intermediate portion which defines a cross-sectional dimension transverse to the longitudinal axis which is greater than respective cross-sectional dimensions of the first and second longitudinal ends of the implant member.

31 Claims, 3 Drawing Sheets

U.S. PATENT DOCUMENTS

| | | | |
|---|---|---|---|
| 5,458,638 A | 10/1995 | Kuslich et al. | |
| 5,489,308 A | 2/1996 | Kuslich et al. | |
| 5,534,031 A | 7/1996 | Matsuzaki et al. | |
| 5,645,596 A * | 7/1997 | Kim et al. | 623/17.16 |
| 5,653,761 A | 8/1997 | Pisharodi | |
| 5,653,762 A | 8/1997 | Pisharodi | |
| 5,658,336 A | 8/1997 | Pisharodi | |
| 5,658,337 A | 8/1997 | Kohrs et al. | |
| 5,669,909 A | 9/1997 | Zdeblick et al. | |
| 5,674,296 A | 10/1997 | Bryan et al. | |
| 5,766,253 A | 6/1998 | Brosnahan, III | |
| 5,782,919 A | 7/1998 | Zdeblick et al. | |
| 5,865,847 A | 2/1999 | Kohrs et al. | |
| 5,876,457 A | 3/1999 | Picha et al. | |
| 5,888,224 A | 3/1999 | Beckers et al. | |
| 5,888,226 A * | 3/1999 | Rogozinski | 623/17.16 |
| 5,895,427 A | 4/1999 | Kuslich et al. | |
| 5,906,616 A | 5/1999 | Pavlov et al. | |
| 5,968,098 A | 10/1999 | Winslow | |
| 6,080,158 A | 6/2000 | Lin | |
| 6,093,207 A | 7/2000 | Pisharodi | |
| 6,123,705 A * | 9/2000 | Michelson | 623/17.16 |
| 6,165,219 A | 12/2000 | Kohrs et al. | |
| 6,482,233 B1 * | 11/2002 | Aebi et al. | 623/17.11 |

* cited by examiner

PRIOR ART
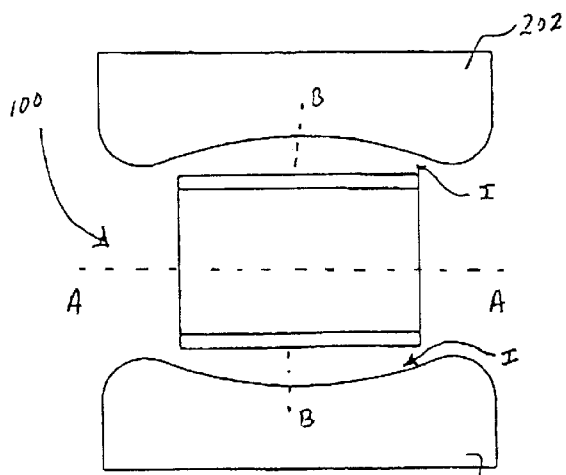
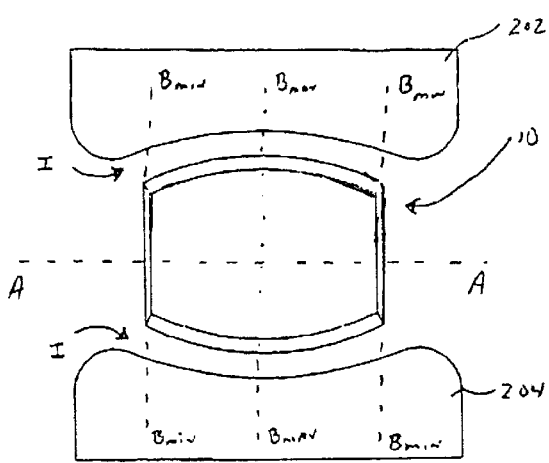
FIG. 6A
FIG. 7A
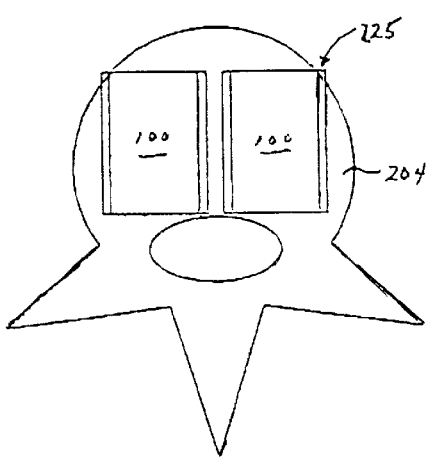
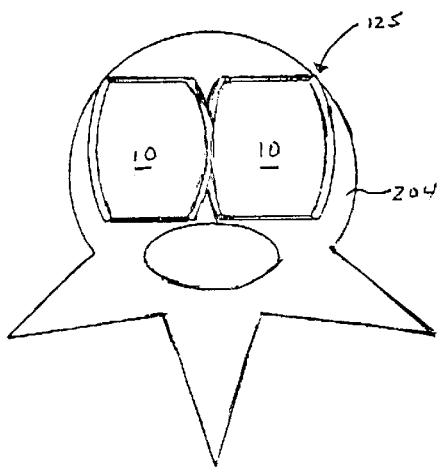
FIG. 6B
FIG. 7B
PRIOR ART

THREADED APPARATUS FOR FUSING ADJACENT BONE STRUCTURE

The present application claims the benefit of U.S. Provisional Application No. 60/242,927 filed Oct. 24, 2000, the disclosure of which is hereby incorporated herein.

BACKGROUND

The present disclosure generally relates to a surgical apparatus for fusing adjacent bone structures, and, more particularly, to a threaded, barrel-shaped apparatus and method for fusing adjacent vertebrae.

The fusion of adjacent bone structures is commonly performed to provide for long-term replacement to compensate for vertebral subluxation typically caused by severe trauma to the spine, degenerative or deteriorated bone disorders, e.g., osteoporosis, abnormal curvature of the spine (scoliosis or kyphosis) and/or weak or unstable spine conditions typically caused by infections or tumors. In addition, an intervertebral disc, which is a ligamentous cushion disposed between adjacent vertebrae, may also undergo deterioration or degeneration as a result of injury, disease, tumor or other disorders. The disk shrinks or flattens leading to mechanical instability and painful disc translocations, commonly referred to as a "slipped disc" or "herniated disc".

Conventional procedures for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony ingrowth or "fusion" with the plug and opposed vertebrae.

Alternatively, at least one metallic fusion cage may be is inserted within a tapped bore or channel formed in the intervertebral space thereby stabilizing the vertebrae and maintaining a pre-defined intervertebral space. A pair of fusion cages may also be implanted within the intervertebral space. After a period of time, the soft cancellous bone of the surrounding vertebral bone structures infiltrates the cage through a series of apertures disposed within its external wall and unites with bone growth inducing substances disposed within an internal cavity to eventually form a solid fusion of the adjacent vertebrae.

SUMMARY

The present disclosure relates to a barrel-like fusion implant apparatus for facilitating fusion of adjacent bone structures. The apparatus includes an implant member which is positioned between adjacent opposed bone structures and which defines a longitudinal axis and first and second longitudinal ends. The implant member includes an outer wall dimensioned to engage the opposed bone structures upon positioning therebetween in supporting relation therewith. The outer wall includes at least one thread for facilitating positioning of the implant member between opposing bone structures. Preferably, the implant member also includes an intermediate portion which defines a cross-sectional dimension transverse to the longitudinal axis which is greater than respective cross-sectional dimensions of the first and second longitudinal ends of the implant member.

The present disclosure also relates to a method of fusing adjacent vertebrae utilizing a barrel-like fusion cage. The method includes the steps of: 1) accessing a space defined between the vertebrae; 2) providing a barrel-like fusion cage as described above; 3) advancing one of the first and second ends of the fusion cage into the space between adjacent vertebrae and positioning the cage in contact with the adjacent vertebrae; and 4) permitting bone ingrowth into contacting surfaces of the fusion cage to facilitate fusion of the adjacent vertebrae.

BRIEF DESCRIPTION OF THE DRAWINGS

Preferred embodiments of the disclosure are described herein with reference to the drawings wherein:

FIG. 6A is a lateral view illustrating a pair of cylindrically-shaped prior art fusion implants positioned within the intervertebral space for fusion of adjacent vertebrae;

FIG. 6B is a top view showing a side-by-side orientation of two prior art cylindrically-shaped fusion cages between two adjacent vertebrae;

FIG. 7A is a lateral view showing the placement of the fusion cage of FIG. 1 between two adjacent vertebrae;

FIG. 7B is a top view showing a pair of fusion implants according to the present disclosure positioned within the intervertebral space for fusion of adjacent vertebrae.

DETAILED DESCRIPTION

Figure 1:
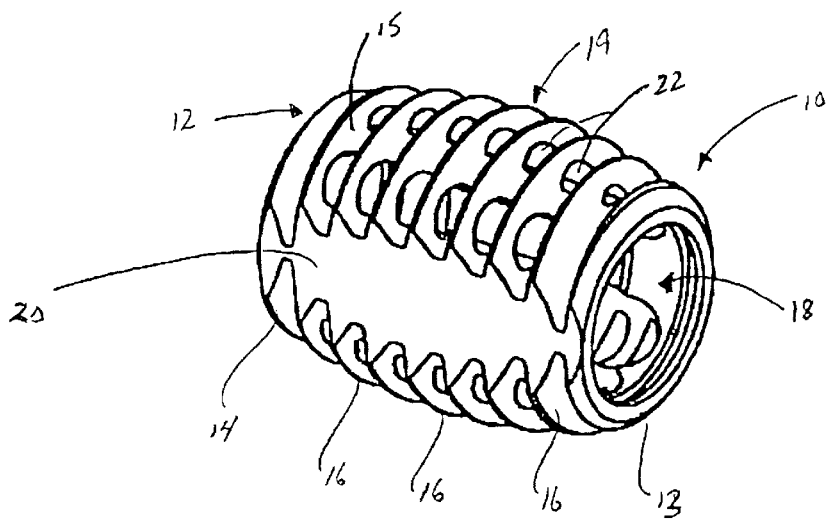
FIG. 1 is a perspective view of a fusion cage according to the present disclosure.

Referring now to the drawings in which like reference numerals identify similar or identical elements throughout the several views, FIGS. 1–5 illustrate the fusion cage implant according to the present disclosure. Fusion cage 10 is contemplated to be a self-tapping implant, i.e., the implant is intended to be inserted within a preformed bore in adjacent bone structures, e.g., adjacent vertebrae, without necessitating tapping of an internal thread within the bone structures prior to insertion. Alternatively, the implant may be inserted within a tapped bore formed in adjacent vertebral bodies as is conventional in the art.

Fusion implant 10 includes a generally elongated body 12 having a proximal end 13 and a distal end 14. In the drawings and in the description which follows, the term "proximal", as is traditional, will refer to the end of the cage 10 which is closer to the surgeon, while the term "distal" will refer to the end which is further from the surgeon. Preferably, cage 10 is fabricated from a suitable biocompatible rigid material such as titanium and/or alloys of titanium, stainless steel, ceramic materials or rigid polymeric materials. Moreover, it is envisioned that cage 10 is sufficient in strength to at least partially replace the supporting function of an intervertebral disc, i.e., to maintain adjacent vertebrae in desired spaced relation, during healing and fusion. Cage 10 is preferably provided in various lengths ranging from about 24 mm to about 28 mm for example.

Figure 2:
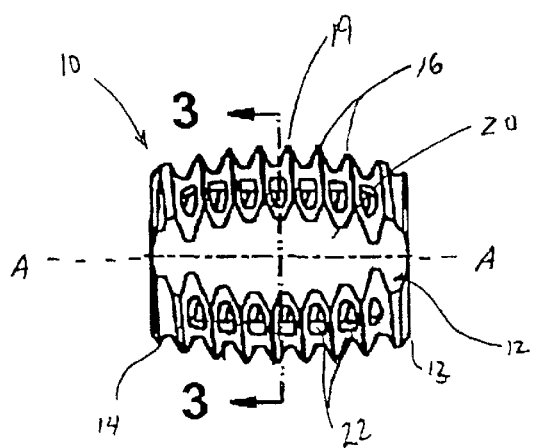
FIG. 2 is a side view of the fusion cage shown in FIG. 1.
Figure 3:
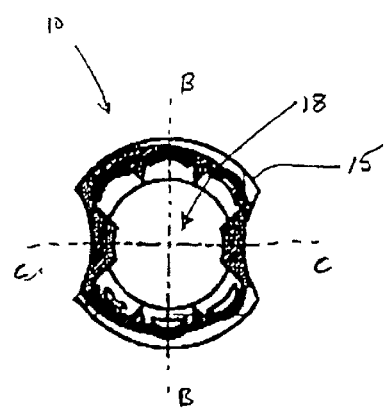
FIG. 3 is a cross-sectional view of the fusion cage taken along section line 3—3 of FIG. 2.

As best shown in FIGS. 1 and 3, the body 12 of cage 10 includes an outer wall 15 which encloses an inner cavity 18 defined within the interior of the cage body 12. Inner cavity 18 accommodates bone chips or bone growth inducing substances as is known in the art to induce the soft cancellous bone surrounding the vertebrae to grow inwardly towards the contact surfaces of the fusion cage 10 to stabilize the cage 10 between two adjacent vertebrae 202, 204 (FIG. 7A). Outer wall 15 is generally barrel-shaped along a longitudinal axis "A" which extends from proximal end 13 to distal end 14 (FIG. 2) and includes a bulge 19 generally positioned midway therebetween. As explained in more detail below, it is envisioned that the barrel-like shape of cage 10 increases the overall strength and load sharing capacity of the cage 10, tends to reduce "stiffness" which has been associated with other prior art designs and allows more bone graft substances to be packed into the augmented internal volume of the cage 10 which will further enhance bone fusion.

Figure 4:
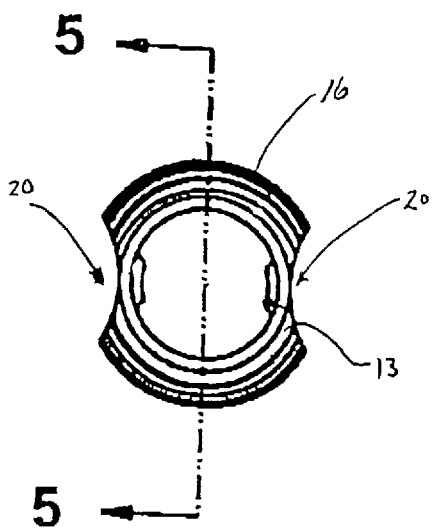
FIG. 4 is an axial view of the fusion cage of FIG. 1.

Outer wall 15 also includes at least one side cut-out or concave wall surface portion 20 (FIG. 3) which extends parallel to longitudinal axis "A" along outer wall 15 generally from the proximal end 13 to the distal end 17. Preferably, two side cut-outs 20 are disposed along outer wall 15 in diametrically opposing relation to reduce the effective dimension or diameter of cage 10 transversally relative to longitudinal axis "A". In either case, the disposition of the side cut-out(s) 20 (FIG. 3) enhance the low profile features of the present disclosure and facilitate insertion between the vertebral bodies 202, 204. With reference to FIGS. 3 and 4, side cut-outs 20 of body 12 provide a generally elliptical configuration or appearance to cage 10 defining a major dimension "B" which is greater than a minor dimension "C". It is envisioned that this configuration provides a greater surface area of the implant so as to facilitate contacting engagement and support of the implant with the adjacent vertebrae 202, 204 (FIG. 7A). The side cut-outs 20 are disposed along the minor axis "C" to enhance the low profile features of cage 10 and facilitate insertion.

Figure 5:
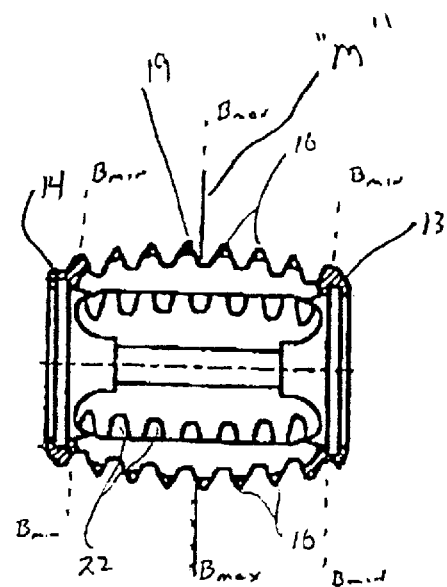
FIG. 5 is a cross-sectional view of the fusion cage taken along section line 5—5 of FIG. 4.

As best shown in FIG. 5, the major dimension "B" along axis "A" varies from a minimum dimension "$B_{min}$" proximate the ends 13, 14 of cage body 12 to a bulge section 19 having a maximum dimension "$B_{max}$" generally disposed midway between ends 13, 14 along a medial axis "M". More specifically, body 12 of cage 10 is symmetrically arranged about medial axis "M" whereby the maximum diameter or cross-sectioned dimension $B_{max}$ extends along or adjacent to the medial axis "M" and progressively decreases to the proximal and distal ends 13, 14 where the cross-sectional diameters or dimensions are substantially equal. As can be appreciated, this gives cage 10 its barrel-like or bulge-like appearance. Preferably, the maximum diameter or dimension "$B_{max}$" ranges from about 12 mm to about 20 mm and the minimum diameter or dimension "$B_{min}$" ranges from about 13 mm to about 19 mm. In the preferred embodiment, the maximum diameter is 17.5 mm and the minimum diameter is 16 mm. The length is 21 mm. Other dimensions are also contemplated. it is envisioned that dimensioning the cage 10 in this fashion has several distinct advantages: 1) the barrel-like cage is an inherently stronger pressure vessel than a simple cylinder design, i.e., the barrel-like cage has a higher compressive strength, exhibits greater resistance to fatigue and possesses a higher yield load; 2) the barrel-like shape promotes a better anatomical fit between adjacent vertebrae 202, 204 in both the transverse plane (Compare FIG. 6B with FIG. 7B) and the sagittal plane (Compare FIG. 6A with FIG. 7A); 3) the low profile ends 13, 14 and the side cut-outs 20 facilitate insertion of the cage 10 and allow two cages 10 to be placed side-by-side with reduced overhang 125 outside the periphery of the vertebral bodies 202 (Compare FIG. 6B with FIG. 7B); and 4) the barrel-like shape of the cage 10 results in an increase in the internal volume of the cage 10 which enables more bone to grow into the cage 10, thus enhancing bone-to-cage fusion. The barrel cage also exhibits a higher expulsion load, i.e., force required to eject the cage from the intervertebral space.

With reference to FIGS. 1, 2 and 5, outer wall 15 also includes an external threaded configuration formed as part of the exterior surface. Preferably, the external threaded configuration of outer wall 15 includes a generally continuous helical thread 16 which assists in advancing cage 10 into a preformed or pre-drilled cavity between adjacent vertebrae 202, 204. Thread 16 provides a varying bite across the cage 10 length to facilitate insertion of the cage 10 and enhance retention of the cage 10 once positioned between the vertebral bodies 202, 204. Thread 16 is generally helical in shape and includes a self-tapping cutting thread, i.e., the threads are capable of deburring bone material during advancement into the performed channel. Preferably, the thread path is curved along both the major dimension "B" and minor dimension "C" which creates a series non-linear thread segments across the cage 10. In some cases it may be preferable to curve the thread 16 only along one of the dimensions, e.g., major dimension "B", depending upon a particular purpose. It is envisioned that the non-linear thread path of the present disclosure will also provide a self-distracting mechanism during the insertion process which is believed to be advantageous to achieving proper disc height. Alternatively, a thread can be tapped in the bone prior to insertion of the cage 10. As stated above, it is envisioned that cage 10 can be dimensioned such that cage 10 is generally symmetrical about axis "A", i.e., front-to-end symmetry, which will permit insertion of the cage 10 from either the proximal or distal end 13, 14, respectively. In some cases, however, threads 16 can be disposed at an angle relative to axis "A" which will also facilitate insertion of the cage 10 between the vertebral bodies 202, 204 and enhance retention of the cage 10 once inserted.

As best shown in FIGS. 1 and 2, a plurality of apertures 22 extend through outer wall 15 of cage body 12. Apertures 22 are preferably formed by broaching grooves in the internal surface of the internal cavity 18. The effect of such broaching is to remove material from the valleys between the threads 16, thus defining the apertures 22. The advantages of such an arrangement promote immediate bone to bone contact between the vertebral bodies 202, 204 and the bone inducing substances packed within the internal cavity 18 of the cage body 12. Such configuration is disclosed in commonly assigned U.S. Pat. Nos. 4,961,740 and 5,026,373, the contents of which are hereby incorporated by reference.

Preferably, apertures 22 are oriented such that when the cage 10 is inserted between vertebrae, a majority of apertures 22 contact the upper and lower vertebral bone structures 202, 204 to encourage bony ingrowth through cage body 12 from the vertebral bone structures 202, 204. Similarly, the side cut-outs 20 of cage body 102 preferably do not include apertures in order to prevent growth of disc material which might interfere with the overall bone fusing process. Apertures 22 are preferably substantially the same in dimension although it is envisioned that the dimensions of the apertures 22 may vary to provide for more or less bone-to-bone contact depending upon a particular purpose.

The present disclosure also relates to a method of inserting the barrel-like fusion cage 10 into an intervertebral space "I" defined between adjacent vertebrae 202, 204. The method discussed hereinafter will generally relate to an open antero-lateral approach for spinal fusion implant insertion. However, as can be appreciated, other spinal implant procedures are also contemplated, e.g., posterior, direct anterior, etc . . . Laparoscopic approaches are also envisioned.

Initially, one lateral side of an intervertebral space "I" between the two vertebral bodies 202, 204 is accessed utilizing appropriate retractors (not shown) to expose the anterior vertebral surface. Thereafter, the retractor is inserted within the intervertebral space "I" from an antero-lateral or oblique position with relation to the vertebral bodies 202, 204. Such an approach provides advantages with regard to avoiding vessels and ligaments.

Upon insertion of the retractor, the vertebral bodies 202, 204 are distracted whereby the retractor becomes firmly lodged within the intervertebral space "I". A drilling instrument is now utilized to prepare the disc space and vertebral bodies 202, 204 for insertion of the fusion cage 10. Preferably, the cutting depth of drilling instrument can be readily adjusted to correspond to the length of the fusion cage 10. As can be appreciated, as the drilling instrument is advanced into the intervertebral space "I", the surrounding soft tissue is sheared and the bone of the adjacent vertebrae 202, 204 is cut thereby forming a bore which extends into the adjacent vertebrae 202, 204.

The fusion cage 10 is then packed with bone growth inducing substances as in conventional in the art and then mounted on an insertion instrument (not shown) and advanced to a position adjacent the vertebral bodies 202, 204. As mentioned above, the non-linear thread configuration of the fusion cage 10 also provides a self-distracting feature which is believed to enhance implantation of the fusion cage 10 and aid in achieving proper disc height.

Preferably, the insertion instrument includes rotational features which, in turn, cause the fusion cage 10 to rotate and bite into the vertebral bodies 202, 204. As mentioned above, it is envisioned that the center thread or bulge 19 as well as the angle of the threads 16 relative to the longitudinal axis "A", will vary the thread 16 bite during the insertion process which facilitates insertion and retention of the cage 10. Moreover, the low profile ends 13 and 14 of cage body 12 as well as the side cut-outs 20 will also facilitate insertion and allow two cages to be placed closer together decreasing the likelihood of cage 10 overhang. Continued rotation of the insertion instrument causes cage 10 to self-tap within the preformed bore. Cage 10 is then released from the mounting instrument which is subsequently removed from the disc area.

Figure 8:
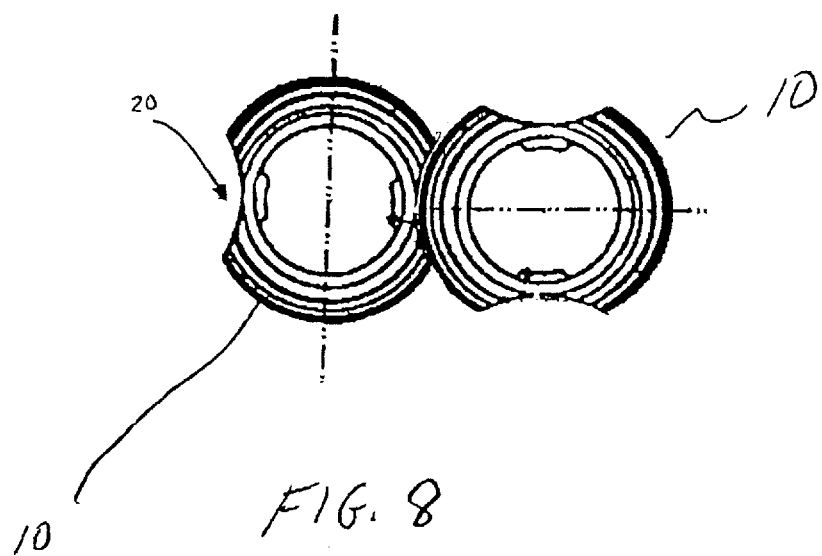
FIG. 8 is an axial view detailing insertion of a pair of the implants within the vertebrae.

Thereafter, a second lateral side of the intervertebral space "I" is accessed and the above-described process is repeated to insert a second cage 10 in lateral side-by-side relation as shown in FIG. 7B. As appreciated, the cages 10 are arranged such that respective side cut-out portions 20 of each cage 10 are disposed in adjacent side-by-side relation. Alternatively, the cages 10 may be positioned such that the curved body 12 of one cage is received within the side cut out 20 of the other cage to further reduce the profile of the implanted cages as depicted in FIG. 8. Such arrangement permits cages 10, 10 to be placed in closer proximity thereby facilitating insertion of the cages 10, 10 within the intervertebral space "I".

Fusion cages 10 form struts across the intervertebral space "I" to maintain the adjacent vertebrae 202, 204 in appropriate spaced relation during the fusion process. Over a period of time, the adjacent vertebral tissue communicates through apertures 22 within cages 10, 10 to form a solid fusion. It is envisioned that the barrel-like shape of each fusion cage 10 is inherently stronger that a cylinder-shaped fusion cage and provides a better anatomical fit between adjacent vertebrae 202, 204 (Compare FIG. 6B with FIG. 7B).

From the foregoing and with reference to the various figure drawings, those skilled in the art will appreciate that certain modifications can also be made to the present disclosure without departing from the scope of the same. For example, it is envisioned that a series of apertures could be drilled at one end of the cage 10 which would allow a surgeon to use a smaller tang and smaller drill thereby preserving more of the posterior elements of the spine during the operation.

While the above description contains many specifics, these specifics should not be construed as limitations on the scope of the disclosure, but merely as exemplifications of preferred embodiments thereof. Those skilled in the art will envision other modifications within the scope and spirit of the claims appended hereto.

What is claimed is:

1. A fusion implant apparatus for facilitating fusion of adjacent bone structures, which comprises:
   an implant member for positioning between adjacent opposed bone structures, the implant member defining a longitudinal axis and first and second longitudinal ends, and having an outer wall dimensioned to engage the opposed bone structures upon positioning therebetween in supporting relation therewith, the outer wall including at least one thread for facilitating positioning between the opposed bone structures, the implant member having an acurate intermediate portion defining a cross-sectional dimension transverse to the longitudinal axis greater than respective cross-sectional dimensions of the first and second longitudinal ends of the implant member.

2. The fusion implant apparatus according to claim 1 wherein the cross-sectional dimension of the implant member progressively increases in an arc from each of the first and second ends toward the intermediate portion.

3. The fusion implant apparatus according to claim 2 wherein the cross-sectional dimensions of the first and second ends are substantially equal.

4. The fusion implant apparatus according to claim 3 wherein the implant member defines a medial transverse axis equidistally disposed between the first and second longitudinal ends and wherein the implant member is symmetrically arranged about the medial transverse axis.

5. The fusion implant apparatus according to claim 4 wherein the implant member defines a substantially circular cross-section.

6. The fusion implant apparatus according to claim 1 wherein the outer wall of the implant member includes at least one concave wall portion extending along the longitudinal axis.

7. The fusion implant apparatus according to claim 6 wherein the outer wall includes diametrically opposed concave wall portions.

8. The fusion implant apparatus according to claim 1 wherein the outer wall defines an internal cavity for reception of bone growth inducing substances.

9. The fusion implant apparatus according to claim 8 wherein the outer wall includes a plurality of apertures extending therethrough in communication with the internal cavity.

10. The fusion implant apparatus according to claim 9 wherein the implant member is dimensioned and configured for insertion between adjacent vertebrae.

11. The fusion implant apparatus according to claim 10 wherein the outer wall of the implant member includes at least one concave wall surface portion extending along the longitudinal axis.

12. The fusion implant apparatus according to claim 11 wherein the outer wall includes diametrically opposed concave wall surface portions.

13. The fusion implant apparatus according to claim 11 wherein the concave wall surface portion is devoid of apertures extending therethrough.

14. The fusion implant apparatus according to claim 1, wherein the implant member is barrel-shaped.

15. A fusion implant apparatus for facilitating fusion of adjacent vertebrae, which comprises:

an implant member dimensioned for positioning between adjacent vertebrae to support the adjacent vertebrae in spaced relation, the implant member defining a longitudinal axis and first and second longitudinal ends, and having an outer wall dimensioned to engage the adjacent vertebrae upon positioning therebetween, the outer wall including at least one thread for facilitating positioning between the adjacent vertebrae and defining a internal cavity for reception of bone growth inducing substances, the implant member having an acurate intermediate portion defining a cross-sectional dimension transverse to the longitudinal axis greater than respective corresponding cross-sectional dimensions of the first and second longitudinal ends of the implant member, the outer wall having a plurality of apertures extending therethrough in communication with the internal cavity to permit fusion of vertebral bone tissue.

16. The fusion implant apparatus according to claim 15 wherein the cross-sectional dimension of the implant member progressively increases in an arc from each of the first and second ends toward the intermediate portion.

17. The fusion implant apparatus according to claim 15 wherein the implant member defines a medial transverse axis equidistally disposed between the first and second longitudinal ends and wherein the implant member is symmetrically arranged about the medial transverse axis whereby a maximum cross-sectional dimension is adjacent the medial transverse axis and whereby the cross-sectional dimension of the implant member progressively decreases in an arc toward each of the first and second longitudinal ends.

18. The fusion implant apparatus according to claim 15, wherein the implant member is barrel-shaped.

19. A method for fusing adjacent vertebrae, comprising steps of:

providing an implant member defining a longitudinal axis and first and second longitudinal ends, the implant member having an acurate intermediate portion defining a cross-sectional dimension transverse to the longitudinal axis greater than respective corresponding cross-sectional dimensions of the first and second longitudinal ends of the implant member;

accessing the intervertebral space defined between adjacent vertebrae;

advancing the implant member within the intervertebral space such that the first and second longitudinal ends are adjacent respective anterior and posterior sections of the adjacent vertebrae; and permitting bone growth into contacting surfaces of the implant member to facilitate of the adjacent vertebrae.

20. The method of claim 19 wherein the implant member includes an exterior wall defining an internal cavity and having apertures extending therethrough and further including the step of permitting bony tissue of the adjacent vertebrae to grow through the apertures to communicate with bone growth inducing substances disposed within the internal cavity.

21. The method of claim 20 wherein the implant member includes an external threaded portion, and wherein the step of advancing includes rotating the implant member about the longitudinal axis such that the threaded portion engages the adjacent vertebrae to facilitate advancement of the implant member within the intervertebral space.

22. The method according to claim 19, wherein the implant member is barrel-shaped.

23. A fusion implant apparatus for facilitating fusion of adjacent bone structures, which comprises:

an implant member for positioning between adjacent opposed bone structures, the implant member defining a longitudinal axis and first and second longitudinal ends, one of such ends being open, and having an outer wall dimensioned to engage the opposed bone structures upon positioning therebetween in supporting relation therewith, the outer wall defining an internal cavity to permit fusion of vertebral bone tissue, said open end being larger than any one of said apertures, the outer wall including at least one thread for facilitating positioning between the opposed bone structures, the implant member having an acurate intermediate portion defining a cross-sectional dimension transverse to the longitudinal axis greater than respective cross-sectional dimensions of the first and second longitudinal ends of the implant member.

24. The fusion implant apparatus according to claim 23 wherein the implant member defines a medial transverse axis equidistally disposed between the first and second longitudinal ends and wherein the implant member is symmetrically arranged about the medial transverse axis.

25. The fusion implant apparatus according to claim 23, wherein the implant member is barrel-shaped.

26. A fusion implant apparatus for facilitating fusion of adjacent vertebrae, which comprises:

an implant member dimensioned for positioning between adjacent vertebrae to support the adjacent vertebrae in spaced relation, the implant member defining a longitudinal axis and first and second longitudinal ends, one of such ends being open, and having an outer wall dimensioned to engage the adjacent vertebrae upon positioning therebetween, the outer wall dimensioned to engage the adjacent vertebrae upon positioning therebetween, the outer wall defining an internal cavity for reception of bone growth inducing substances, the outer wall including at least one thread for facilitating positioning between the opposed bone structures, the implant member having an acurate intermediate portion defining a cross-sectional dimension transverse to the longitudinal axis greater than respective corresponding cross-sectional dimensions of the first and second longitudinal ends of the implant member, the outer wall having a plurality of apertures extending therethrough in communication with the internal cavity to permit fusion of vertebral bone tissue, said open end being larger than any one of said apertures.

27. The fusion implant apparatus according to claim 26 wherein the cross-sectional dimension of the implant member progressively increases from each of the first and second ends toward the intermediate portion.

28. The fusion implant apparatus according to claim 27 wherein the implant member defines a medial transverse axis equidistally disposed between the first and second longitudinal ends and wherein the implant member is symmetrically arranged about the medial transverse axis whereby a maximum cross-sectional dimension is adjacent the medial transverse axis and whereby the cross-sectional dimension of the implant member progressively decreases toward each of the first and second longitudinal ends.

29. The fusion implant apparatus according to claim 26, wherein the implant member is barrel-shaped.

30. A method for fusing adjacent vertebrae, comprising the steps of:

providing a threaded implant member defining a longitudinal axis and first and second longitudinal ends, one of such ends being open, the implant member having an acurate intermediate portion defining a cross-sectional dimension transverse to the longitudinal axis greater than respective corresponding cross-sectional dimensions of the first and second longitudinal ends of the implant member;

accessing the intervertebral space defined between adjacent vertebrae;

advancing the implant member within the intervertebral space such that the first and second longitudinal ends are adjacent respective anterior and posterior sections of the adjacent vertebrae; and permitting bone growth into contacting surfaces of the implant member to facilitate fusion of the adjacent vertebrae.

31. The method of claim 30 wherein the implant member includes an exterior wall defining an internal cavity and having apertures extending therethrough and further including the step of permitting bony tissue of the adjacent vertebrae to grow through the apertures to communicate with bone growth inducing substances disposed within the internal cavity, said open end being larger than any one of said apertures.

* * * * *

UNITED STATES PATENT AND TRADEMARK OFFICE
CERTIFICATE OF CORRECTION

PATENT NO. : 6,726,722 B2  Page 1 of 1
DATED : April 27, 2004
INVENTOR(S) : Jared Walkenhorst, Herb Cohen and Lance Middleton It is certified that error appears in the above-identified patent and that said Letters Patent is hereby corrected as shown below:

Column 1,
Line 34, cancel "is".

Column 2,
Line 62, after "28 mm" insert -- , --.

Column 3,
Line 23, "enhance" should read -- enhances --.
Line 24, "facilitate" should read -- facilitates --.
Line 53, "it" should read -- It --.

Column 4,
Line 18, after "series" insert -- of --.

Column 7,
Line 15, "a" should read -- an --,
Lines 17 and 44, "acurate" should read -- arcuate --.
Line 40, after "comprising" insert -- the --.
Line 57, after "facilitate" insert -- fusion --.

Column 8,
Lines 18 and 44, "acurate" should read -- arcuate --.

Column 9,
Line 6, "acurate" should read -- arcuate --.

Signed and Sealed this

Thirty-first Day of August, 2004

JON W. DUDAS
*Director of the United States Patent and Trademark Office*